United States Patent
Massaro

(10) Patent No.: US 7,876,935 B2
(45) Date of Patent: Jan. 25, 2011

(54) SAMPLE PROCESSING APPARATUS WITH A VISION SYSTEM

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 1364 days.

(21) Appl. No.: 11/342,504

(22) Filed: Jan. 30, 2006

(65) Prior Publication Data

US 2007/0177778 A1    Aug. 2, 2007

(51) Int. Cl.
    *G06K 9/00*    (2006.01)
(52) U.S. Cl. .................................... 382/128
(58) Field of Classification Search .............. 382/128
    See application file for complete search history.

(56) References Cited

U.S. PATENT DOCUMENTS

| | | | |
|---|---|---|---|
| 4,399,711 A | 8/1983 | Klein | |
| 4,944,922 A | 7/1990 | Hayashi | |
| 5,096,353 A | 3/1992 | Tesh et al. | |
| 5,141,871 A | 8/1992 | Kureshy et al. | |
| 5,275,951 A * | 1/1994 | Chow et al. | 436/50 |
| 6,226,081 B1 * | 5/2001 | Fantone et al. | 356/239.6 |
| 6,456,944 B1 | 9/2002 | Burkhardt et al. | |
| 2002/0094578 A1 | 7/2002 | Kowallis et al. | |
| 2004/0023223 A1 * | 2/2004 | Thompson et al. | 435/6 |
| 2004/0089051 A1 * | 5/2004 | Camenisch | 73/1.05 |
| 2004/0110212 A1 | 6/2004 | McCormick et al. | |
| 2005/0096528 A1 * | 5/2005 | Fritz et al. | 600/407 |
| 2005/0163354 A1 * | 7/2005 | Ziegler | 382/128 |
| 2006/0105453 A1 * | 5/2006 | Brenan et al. | 435/325 |
| 2007/0208454 A1 * | 9/2007 | Forrester et al. | 700/216 |
| 2009/0055131 A1 * | 2/2009 | Bukshpan et al. | 702/187 |

FOREIGN PATENT DOCUMENTS

| | | |
|---|---|---|
| EP | 0185330 A2 | 4/1980 |
| WO | WO 03/100442 A1 | 12/2003 |
| WO | WO 2006/036307 A2 | 4/2006 |

OTHER PUBLICATIONS

International Search Report and Written Opinion for International Application No. PCT/US2007/002404 dated Jul. 25, 2007.

* cited by examiner

*Primary Examiner*—Bhavesh M Mehta
*Assistant Examiner*—Nirav G Patel
(74) *Attorney, Agent, or Firm*—Wolf, Greenfield & Sacks, P.C.

(57) ABSTRACT

A sample processing apparatus has an associated machine vision system. The vision system may acquire an image of at least one fluidic chamber, which can be analyzed by the machine vision system and/or stored. The image and/or analysis of the image may provide a record of the actions of the sample processing apparatus, which permits a user to verify proper operation of the sample processing apparatus.

18 Claims, 6 Drawing Sheets

SAMPLE PROCESSING APPARATUS WITH A VISION SYSTEM

BACKGROUND OF INVENTION

1. Field of Invention

This invention relates to a sample processing apparatus with a vision system.

2. Discussion of Related Art

Sample processing apparatus are used to automatically manipulate sample holders and precise amounts of fluid. These devices enable testing and analysis of samples in many fields, such as genomics, drug discovery, proteomics, and diagnostics. For example, a blood sample may be aspirated by a pipettor or other liquid handling device, moved and dispensed at another location. The sample may be mixed with other compounds, filtered, centrifuged or otherwise processed as part of an analysis protocol.

SUMMARY OF INVENTION

In one aspect of the invention, a sample processing apparatus comprises a vision system that allows for the verification at least one aspect of a sample handling process involving a change in state of a sample with respect to a sample holder or other fluidic chamber. For example, the vision system may allow for the verification of a pipette aspiration/dispensing operation, a sample filtering operation or other with respect to a sample.

In another aspect of the invention, a vision system associated with a sample processing apparatus may capture and analyze images that are each associated with steps in a sample handling procedure. For example, an image of a sample holder supporting a liquid sample may be captured before a process, e.g., to verify that the liquid sample was present. Another image of the sample holder may be captured after the process has been completed, e.g., to verify that at least some portion of the liquid sample has been moved relative to the sample holder. For example, during a pipetting operation, a first image may be used to verify that a first volume of liquid sample is present in a pipette tip. After a dispensation operation, a second image may be used to verify that a second volume of the liquid sample (smaller than the first volume) remains in the tip. Thus, in this example, the vision system may be used to verify a change in volume of the sample with respect to the sample holder, i.e., verify a change in state of the sample with respect to a fluidic chamber. In some embodiments, such an arrangement may reduce or eliminate a need for individual sensors for each sample holder (such as capacitive sensors for detecting fluid in each of a plurality of pipette tips) to determine the presence, absence, movement, color, position, or other change in state of a sample. Instead, one or more images captured by the vision system may be used to assess multiple samples associated with multiple sample holders. In some embodiments, the vision system may be used for multiple purposes in addition to capturing and/or analyzing images relating to liquid samples. For example, the vision system may be used to control the operation of a robotic device, such as providing position feedback for a robotic manipulator.

In yet another aspect of the invention, a machine vision system may capture images of at least a portion of a sample processing apparatus during a procedure and analyze the captured image. The analysis may provide a user with information necessary to determine if and when an error occurred and/or to verify that the procedure was performed correctly.

In still another aspect of the present invention, images captured by a vision system associated with a sample processing apparatus may be tagged with an identifier or otherwise associated with a particular identity. For example, one or more images captured by a vision system may be associated with processing of a particular liquid sample that was taken, at least in part, from a particular person. The images may be associated with an identifier (e.g., a unique string of alphanumeric text) that has been provided for the liquid sample. Thus, the images may be later associated with the liquid sample and the person from whom the sample was taken. This may allow the person or some other entity to verify that particular processes were performed on the sample.

One aspect of the invention provides a method for monitoring a sample handling process including associating a liquid sample with a fluidic chamber (such as a pipette tip or well in a multi-well plate), and performing a sample handling process with the liquid sample with respect to the fluidic chamber. The sample handling process may include a change in state of the liquid sample with respect to the fluidic chamber, such as a change in color, position, volume or other characteristic of the sample. A machine vision system may be used to acquire a 2-dimensional image of at least a portion of the fluidic chamber before, during or after performance of the sample handling process, and the acquired image may be stored to allow later verification of the change in state of at least a portion of the liquid sample during the sample handling process.

In another aspect of the invention, a sample handling apparatus may include at least one fluidic chamber adapted to hold a liquid sample and allow for a change in state of the liquid sample relative to the fluidic chamber. A machine vision system may have an image acquisition device positioned to acquire a 2-dimensional image of at least a portion of the fluidic chamber, and be adapted to allow verification of the change in state of the liquid sample relative to the at least one fluidic chamber based on the image.

These and other aspects of the invention will be apparent from the following description and claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
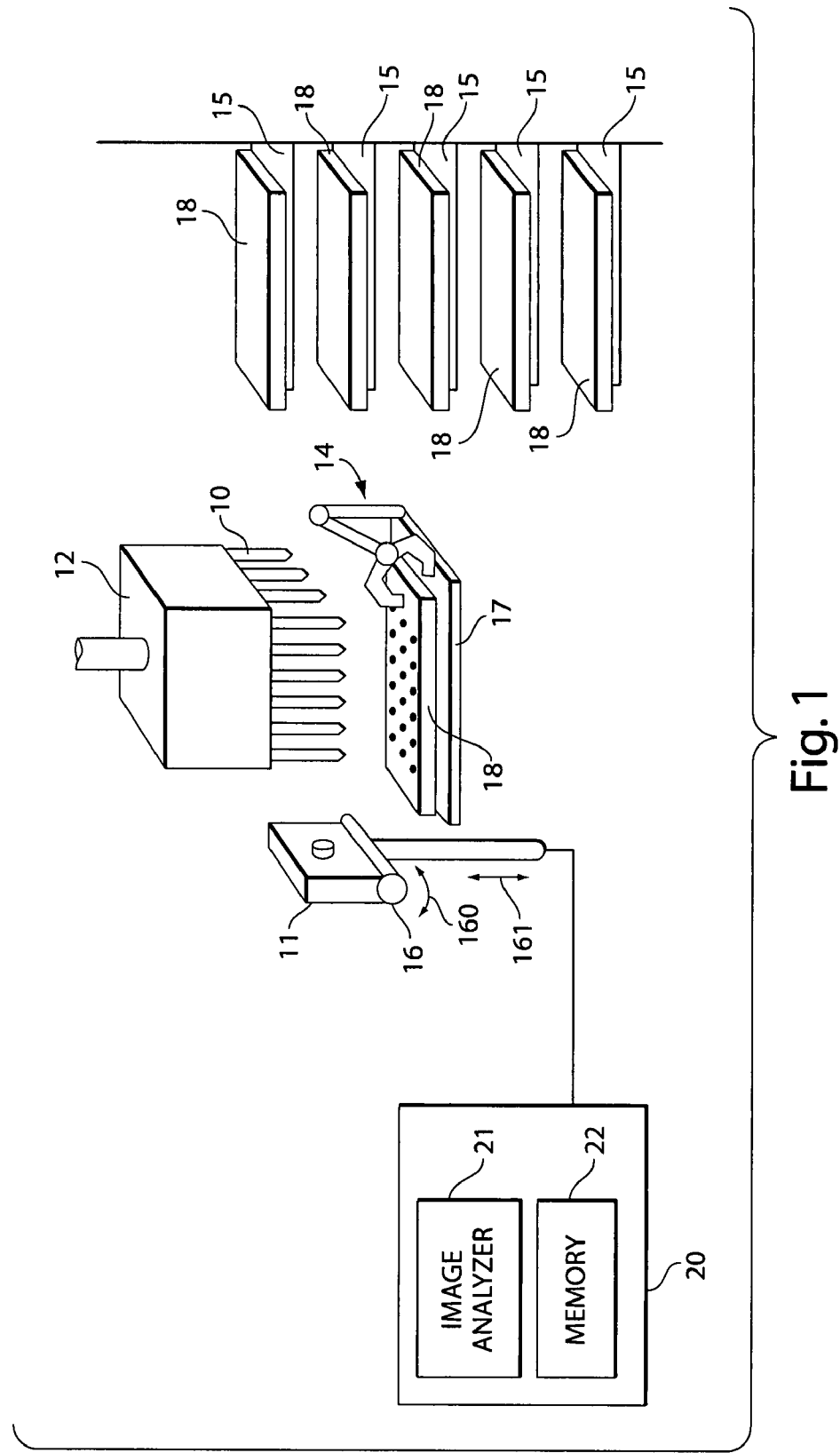
FIG. 1 is a perspective view of a sample processing apparatus according to one embodiment of the present invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

As discussed above, sample processing apparatus are used to manipulate fluid samples so that various processes may be performed using the samples, such as pipetting, centrifuge processing, mixing, filtering, electrophoretic gel separation, passage through microfluidic channels, and so on. These processes may be performed automatically and concurrently on a plurality of samples, enabling high throughput and rapid testing protocols. However, sometimes a device may malfunction during the sample processing. For example, a pipette may not aspirate or dispense a sample, may clog, or may aspirate an air bubble. A sample tray may be placed in a suboptimal location, a centrifuge may not spin long or fast enough, or a plate may not be properly washed. Any of these errors may lead to inaccurate or misleading results.

One aspect of the present invention relates to a sample processing apparatus with an associated machine vision system that may be used to verify the proper operation of a sample process, such as a transfer of a liquid sample from one sample holder to another. Some examples of sample holders (or fluidic chambers) include pipettes, tubes (e.g., centrifuge tubes, sample tubes, and capillary tubes), syringes, fluidic channels and plates (e.g., filter plates and sample well plates). The machine vision system may include an image acquisition device arranged to capture a 2-dimensional image that includes at least a portion of a sample holder. After the image acquisition device captures an image of the sample holder, the image can be stored and/or analyzed to confirm that movement or other change in state of the sample was performed properly. In order to facilitate identification and retrieval, an image can be associated with one or more samples when the image is stored or at the time of capture, e.g., associated with an identifier that corresponds to the sample. Alternatively or additionally, data extracted from an image (or learned from other analysis of the image) may be tagged with an identifier and stored. Image analysis may include cutting portions of an image, annotating an image, comparing two or more images to each other, assessing a physical condition represented in the image (such as estimating a volume of sample in a holder using image information), or other. Image analysis may be performed in a fully automatic way, such as by image analysis software, or by interaction of a user with the image analyzer. For example, the image analyzer may present one or more images for review by a user, who may assess one or more conditions shown in the image(s) and provide information to the image analyzer regarding the assessment.

The machine vision system can be configured to extract different types of data from an image. For example with respect to a pipette tip, the machine vision system may verify proper aspiration, complete dispense, the volume aspirated, the absence of bubbles and/or clots in the pipette, the presence of a filter during aspiration, proper positioning of a sample well tray, etc. This flexibility allows a machine vision system to replace or supplement a number of instruments and/or sensors. Instead of requiring a pressure sensor to detect clots and a UV absorbance or fluorescence measurement system to determine concentration, a single machine vision system may be able to extract both pieces of data. This may reduce the space requirements and cost of a sample processing apparatus without sacrificing accuracy.

Additionally, the machine vision system may easily accommodate many different fluidic chambers, regardless of shape, size, or orientation. The vision system may be able to capture and analyze one or more images of a centrifuge tube, a pipette (regardless of size), a sample well plate, or other, in some cases without the need to make significant alteration to the system. Alternatively or additionally, the vision system can include image analysis capabilities to determine different characteristics in different fluidic chambers, such as the volume in a centrifuge tube, absence of clots in a pipette, proper dispense into a sample well, and presence of sample on an agarose gel.

The ability to store an image and analyze it later permits a user to retrieve additional information even after the sample handling process is complete. For example, a sample processing apparatus may image a sample holder after aspiration and verify that some sample has been aspirated. However, after the procedure is complete, a user may decide that he wants to calculate the volume aspirated, check for bubbles and/or clots in the sample, and confirm the presence of a filter. By recalling the image taken during aspiration, the user may be able to extract the additional desired information even though sample processing is complete.

In this way, machine vision can provide an accurate way to determine whether a sample handling error occurred and where it occurred when the result of a test or procedure seems erroneous. Instead of having to retest samples whenever results are called into question, the vision system may automatically keep a visual record of each sample tested at different stages in processing. Additionally, the machine vision system may give a user the flexibility to choose the timing and number of image acquisitions. A user may choose to record a single time point or multiple time points during a single sample handling process. Furthermore, the ability to tag the image and/or data with an identifier enables a user to quickly group together results from a single patient, sample, and/or record, and to quickly search obtain desired information.

As shown in FIG. 1, a sample processing apparatus 1 according to one embodiment of the present invention includes one or more fluidic chambers or sample holders, such as a pipette tip 10, a well in a multi-well plate 18, or other device arranged to support a liquid sample in some way. Sample holders may be manipulated for use with the apparatus 1 in any suitable way. For example, a multi-channel pipetting head 12 may be arranged to support and/or actuate some or all of the pipette tips 10, e.g., such that a plurality of the tips 10 can be moved together from a first position to a second position and actuated to aspirate and/or dispense a liquid sample. The pipetting head 12 may itself be manipulated by a robotic device or other arrangement that is adapted to support, move and/or actuate the pipetting head 12. Other arrangements may be incorporated into the apparatus 1 for manipulating sample holders 10, such as a robotic manipulator 14 that is capable of moving a sample holder from a storage location to an active location. For example, the robotic manipulator 14 may move a sample well plate 18 from a storage rack 15 to a location 17 where sample can be placed in/removed from the sample well plate 18. The robotic manipulator 14 may include a robotic arm or other suitable apparatus and may have one or more degrees of freedom. In addition, the robotic manipulator 14 may be adapted to engage with and manipulate the pipetting head 12 or other tools in the apparatus 1.

The sample processing apparatus 1 may include a controller 20 that coordinates or otherwise controls operation of various portions of the sample processing apparatus 1, such as the pipetting head 12, manipulator 14, or other portions of the apparatus 1. Additionally, the controller 20 may have a machine vision system that includes an image acquisition device 11 and an image analyzer 21. The image acquisition device 11 may be constructed and arranged to image at least a portion of one or more sample holders that contains a sample during processing of one or more samples associated with the holders. In one embodiment, the image acquisition device may include a camera, e.g., include a CCD imaging device, or other device suitable for capturing an image using visible or other electromagnetic radiation. The image acquisition device 11 may be capable of capturing images in rapid succession to record a movie clip, and/or may be capable of capturing still images.

In one embodiment, the image analyzer 21 may be used to analyze an image captured by the image acquisition device 11, e.g., used to detect any of a number of conditions and/or characteristics of the image. For example, the image analyzer 21 may be used to determine the presence or absence of sample in a sample holder. The image analyzer 21 may also be used to estimate the volume of sample in a sample holder by interpolating indicia on a sample holder or calculating the volume based on the height of a meniscus. The image analyzer 21 may also be used to detect clots or bubbles in a liquid sample, such as by observing a darker or lighter areas in a sample holder. Alternatively or additionally, the image(s) may be used to verify that a process was done correctly. For example, an image may be used to verify that a filter was used during aspiration. Such image analysis may be done automatically, e.g., by a software module operating on a computer or other data processing apparatus, and/or by inputting information from a user in response to review of a displayed image. In addition to providing information regarding image analysis, a user can provide other information that is associated with the image and/or a corresponding sample, such as providing annotations to otherwise unrecorded processing conditions. This information may be stored in a memory 22 with the image and/or with other information relating to the sample.

Figure 2:
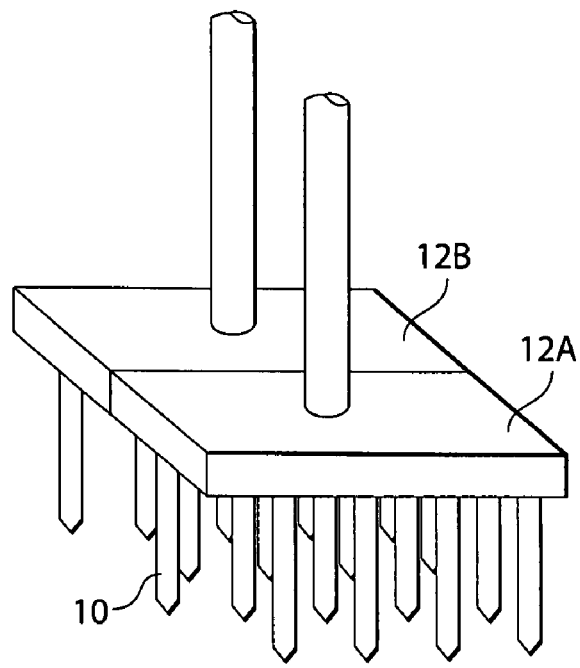
FIG. 2 is a perspective view of a support and sample holders according to one embodiment of the present invention.
Figure 3:
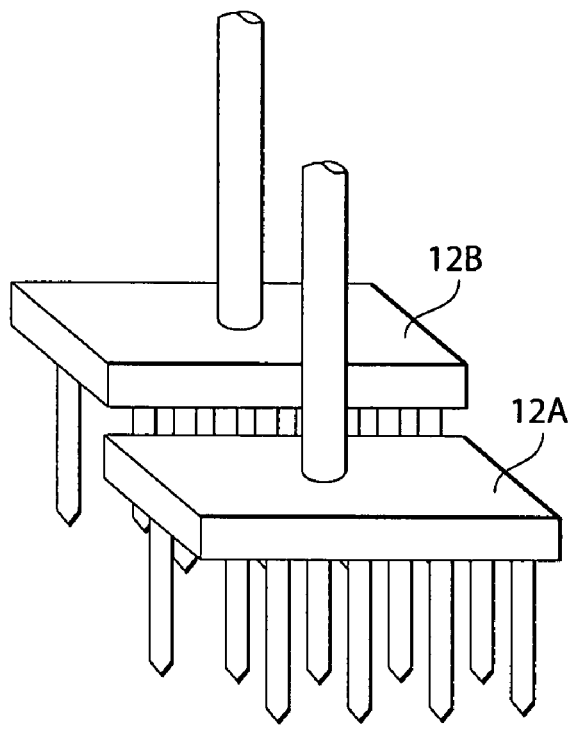
FIG. 3 is a perspective view of the support and sample holders depicted in FIG. 2, where one of the supports has been lowered.

In some applications, the sample holders may be arranged in large groups which may make them difficult to image. For example, sample holders in the form of pipette tips 10 may be arranged in a plurality of columns and rows, as shown in FIG. 2. In this case, the image acquisition device 11 may image a subset of the sample holders. For example, pipetting head 12 may have a plurality of supports 12A, 12B, each of which may carry at least one pipette tip 10. As shown in FIG. 3, the supports 12A, 12B may be moved independently of each other. A first support 12A may lower its respective subset of pipettes while the remainder of the pipettes (e.g., those mounted to a second support 12B) remain in the raised position. If the image acquisition device 11 is positioned to acquire an image of pipettes in the lowered position, the sample processing apparatus 1 may lower the first support 12A so that the image acquisition device 11 may acquire an image of those sample holders 10. Then, the sample processing apparatus 1 may retract the first support 12A and lower the second support 12B to acquire an image of the sample holders connected to the second support 12B. The vision system can thus operate such that all pipette tips 10 having an associated sample are imaged. As will be understood by those of skill in the art, images may alternatively or additionally be acquired when the supports 12A, 12B are in the raised position, or any other position, as long as the image acquisition device 11 can capture a suitable image. Even though FIGS. 2 and 3 depict two supports 12A, 12B, any number of supports 12 may be used. Additionally, FIGS. 2 and 3 depict two offset rows of sample holders 10 on a single support 12A, 12B. However, as will be apparent to one of skill in the art, a single row of sample holders or any number of rows of sample holders may be arranged on a single support, as long as the desired image acquisition can be obtained.

Figure 4:
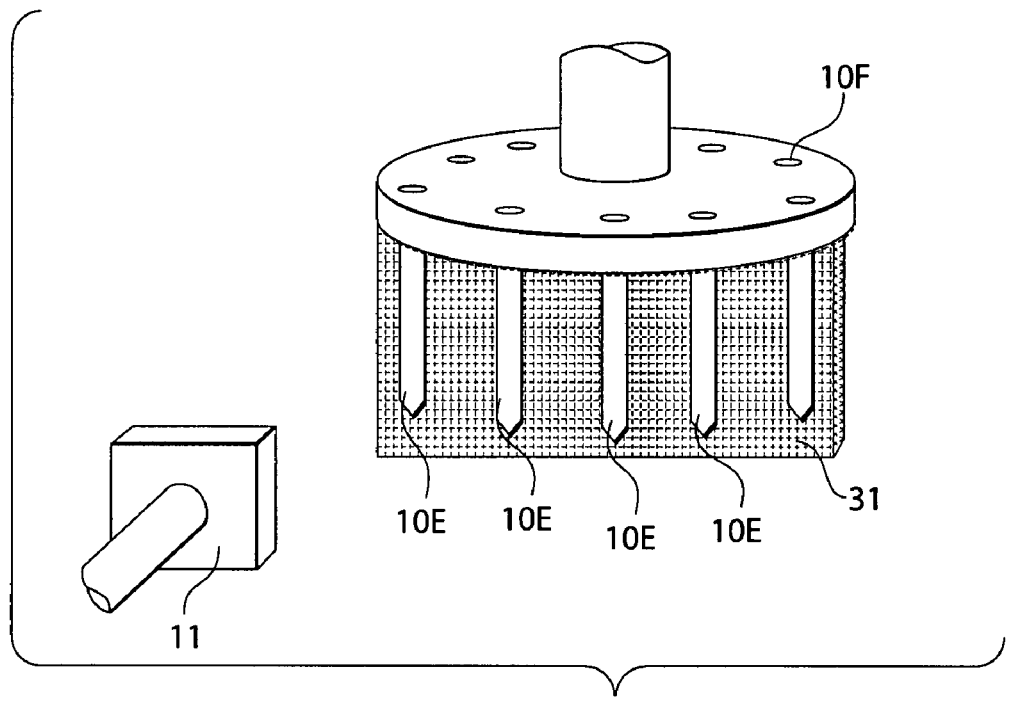
FIG. 4 is a perspective view of a set of sample holders on a support according to another embodiment of the present invention.
Figure 5:
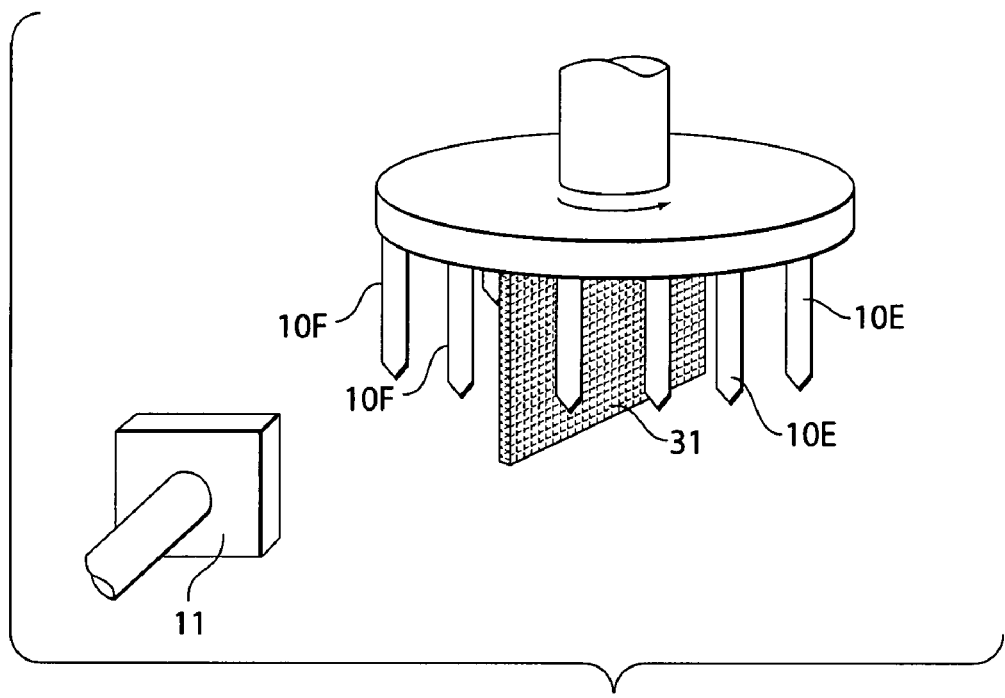
FIG. 5 is a perspective view of the sample holders and support depicted in FIG. 4, where the support has rotated.

Alternative sample holder configurations are also within the scope of the present invention, e.g., sample holders may be arranged in a polygon or a circle like that shown in FIGS. 4 and 5. In order to image all the sample holders, an image acquisition device 11 may image half of the sample holders at a time. For example, a screen 31 may to obstruct the view of a subset of sample holders 10F so as to capture a clear image of the remaining sample holders 10E. After an image is captured of a subset of the sample holders 10E, the support 12 could be rotated as shown in FIG. 5. Once the support has been rotated, the image acquisition device 11 can capture the remaining subset of the sample holders 10F. As will be apparent to one of skill in the art, other sample holder and imaging configurations are possible.

The image acquisition device 11 may be movable to capture images of different areas of the sample processing apparatus 1. For example, the image acquisition device 11 may be movable to acquire an image of one or more sample holders that could otherwise not be obtained without movement of the sample holder. Referring to the illustrative embodiments of FIGS. 2-5, instead of moving the sample holders 10 for imaging, the image acquisition device 11 may be moved or otherwise operated so as to obtain the desired images. The capability to acquire images of different areas may be accomplished by using an image acquisition device with a large field of view or, as shown in FIG. 1, by having a manipulator 16 to position the image acquisition device 11 appropriately. The manipulator 16 may be able to tilt the image acquisition device 11 as shown by arrows 160, raise and lower the image acquisition device as shown by arrows 161, or otherwise move the image acquisition device 11 in any suitable way. The manipulator 16 may be of any design, as long as it can move the image acquisition device 11 in the desired direction(s). Alternatively or additionally, mirrors, lenses, or other optical devices (not shown) may be used to change the field of view of the image acquisition device 11. For example, the sample processing apparatus may move a lens up to the image acquisition device's field of view in order to change the focal length of the image acquisition device 11. (Alternately, the image acquisition device 11 may have a built-in zoom function.) Also, multiple image acquisition devices may be used to obtain visual images of different areas, especially if simultaneous images are desired. Other means to change the field of view for the image acquisition device would be apparent to one of skill in the art and are also within the scope of the present invention. Despite the above, the image acquisition device 11 may be made stationary with a fixed (or variable) field of view.

Figure 6:
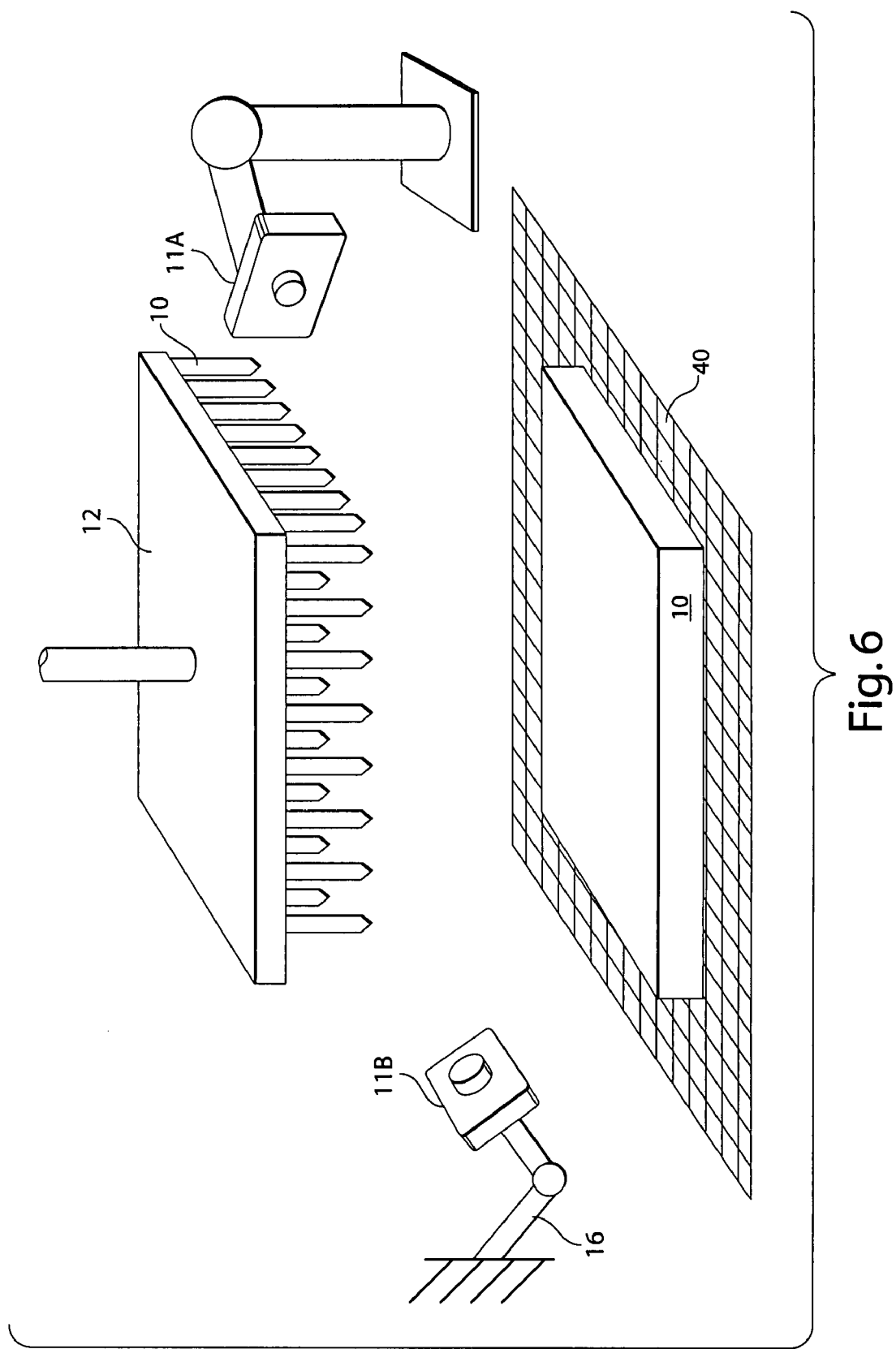
FIG. 6 is a perspective view of a sample processing apparatus according to another embodiment of the present invention.

The machine vision system can also be used to control the operation of portions of the sample processing apparatus 1 other than the image acquisition device 11. For example, as shown in FIG. 6, the machine vision system can be used to appropriately position two sets of sample holders relative to each other for transfer of samples from one holder to another. In this illustrative embodiment, a sample tray 18 may be placed on a surface with a grid 40 on it, and a camera 11A that is part of the image acquisition device 11 may image the sample tray 18 and determine the location of the tray 18 using the grid 40 information. The machine vision system may include a second camera 11B to image the location of pipette tips 10 on the pipetting head 12. The location of the tray 18 and the tips 10 may be used by the sample processing apparatus to determine the relative position of the two so that the head 12 may be moved to suitably locate desired tips 10 relative to wells in the tray 18. The use of machine vision systems for such control is well known in the art, and is not described further herein. Of course, it will be understood that the machine vision system may be used to control other portions of the sample processing apparatus 1, including portions that are not associated with a sample holder.

Additionally or alternatively, the sample holder may include at least one light source, such as a laser, that is aimed at a precise location if the sample holder is in the desired location (not shown). For example, lasers could be configured to shine at the corners of a sample tray. The image acquisition device could capture an image of the tray when properly placed to record that the tray was correctly positioned.

Figure 7:
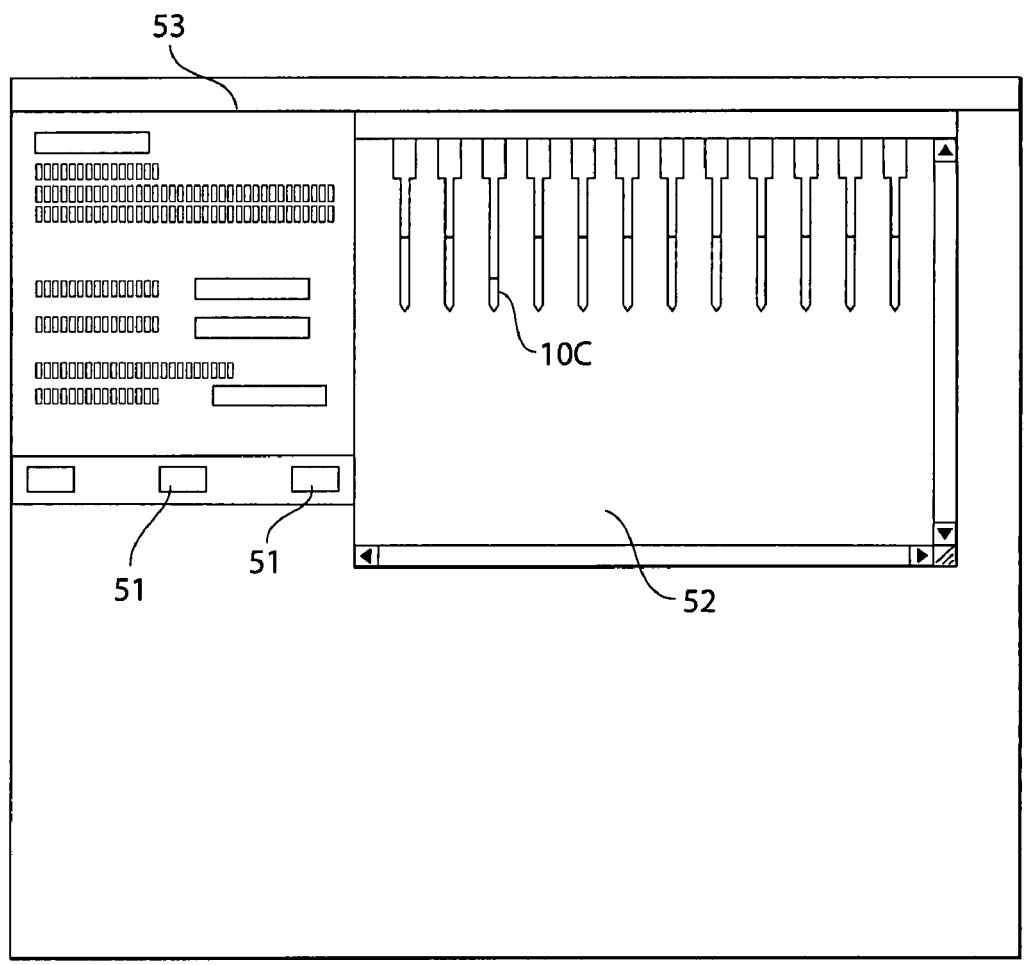
FIG. 7 is a frontal view of a sample graphical user interface according to one embodiment of the present invention.

The controller 20 may have a user interface so that a user can interact with the controller and the sample processing apparatus 1. In one embodiment, the controller may include a computer system, which provides a user interface including a keyboard, mouse or other user pointing device, touch screen, display, printer and/or other components. In one embodiment of the invention, the user interface may include a graphical user interface (GUI) by which the user may receive information from, and input information to, the controller 20. FIG. 7 shows an illustrative embodiment of a GUI which may be included in one embodiment of the present invention. In particular, the GUI may enable the user to activate one or more analysis features of the image analyzer with respect to a given image (or images) 52, or portion of an image, e.g., by clicking or otherwise selecting one or more function buttons 51. For example, if an image 52 shows that the volume of one sample holder 10C is relatively low, a user may control the image analyzer 21 to determine a volume of sample in a sample holder of interest 10C. Image analysis may be done using a single image, or using two or more images. Alternately, the image analyzer could be configured to automatically perform image analysis on captured images, e.g., automatically compute a sample volume for samples included in the image. Results of such analysis may be displayed along with other information 53 and the image 52. The displayed information 53 may include information about the image, samples shown in the image, a patient associated with one or more samples in the image, protocols used to process the samples, or other. A user may be permitted (e.g., by using the GUI) to alter and/or add to the information 53 as desired, e.g., to provide comments regarding a particular sample, processing conditions not recorded in the image, and so on. In addition, the user may be permitted to associate the image with one or more identifiers, such as a patient identity, a source of one or more samples shown in the image, a protocol used to test the sample, etc. The image 52 and associated information 53 may be stored in a database or other suitable store for later reference or other use.

A user may also be able to program the sample processing apparatus or otherwise alter operating instructions used by the controller through the GUI, e.g., specifying the actions of the pipetting head 12, robotic manipulator 14, and manipulator 16; the volume of sample aspirated and/or dispensed; and/or other actions. The operator may additionally be able to program when and what to capture with the image acquisition device, how to tag and/or store the images, and any image analysis to be performed. The user interface may additionally or alternatively comprise buttons, dials, or other non-GUI means that will be apparent to those of skill in the art.

Figure 8:
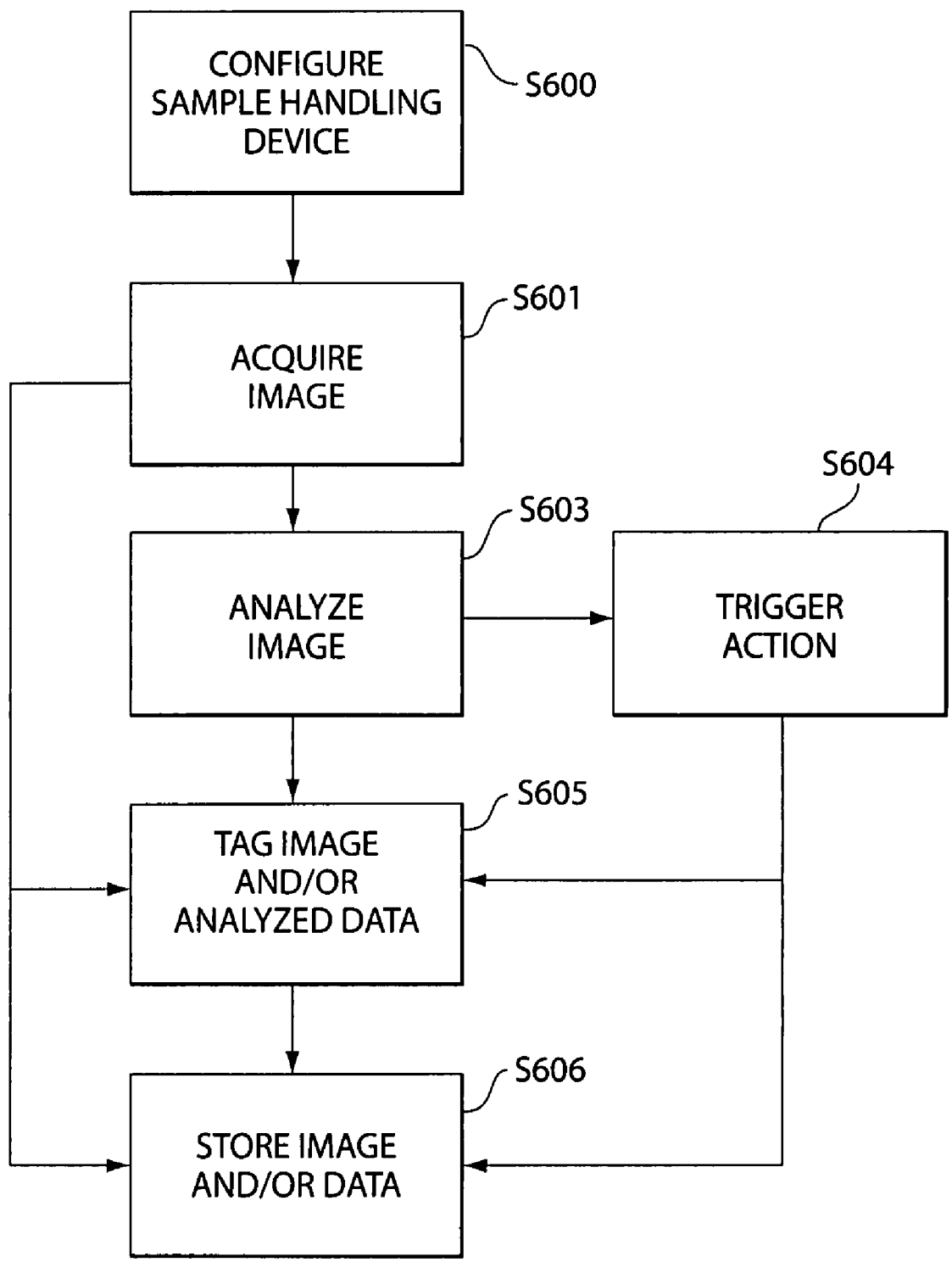
FIG. 8 is a block diagram of an operating procedure according to one embodiment of the present invention.

As shown in FIG. 8, a user may configure a sample processing apparatus to perform a sample handling process, which may include filtering, aspirating, dispensing, centrifuging, microfluidic processes, cell plating, running a gel or other processes with respect to one or more liquid samples. As one example, the sample handling process may be used to test one or more samples for a particular protein or DNA sequence. In step S601, the controller of the sample processing apparatus may direct a machine vision system to acquire an image of a sample or sample holder at a certain point in the process. After the image is acquired, in step S603 the image may be analyzed. For example, an image analyzer may determine a change in state of the sample, e.g., estimate a sample volume in a sample holder, determine a change in volume of the sample, determine a color or change in color of the sample, determine a position or change in position of the sample, check for the presence or absence of sample in a sample holder, or evaluate some other characteristic. In step S605, the results of the analysis and/or the image may be tagged with an identifier so that the image may be associated with the proper sample(s). The identifier tag may comprise alphanumeric symbols, an optical code such as a bar code, or any other identifier, and the identifier may be unique as compared to at least some other identifiers used with other images. In step S606, the image analysis data and/or image may be stored for later retrieval. Alternatively, the image may be stored only if the analysis indicates that an error occurred.

In some applications, it may not be desirable to analyze the image immediately upon capture. In these cases, after the image is acquired, it may be tagged and stored. As described above, the image can be tagged with a batch number, sample number, patient number, or any other identifier.

Additionally or alternatively, the results of the image analysis may trigger some action by the sample processing apparatus, e.g., in step S604. For example, if the analysis reveals that a sample was improperly or incompletely aspirated, the sample processing apparatus 1 may stop, sound an alarm, and/or reattempt the aspiration. Failed sample processes may prompt a sample to be reprocessed or discarded. The sample processing apparatus 1 may alternatively or additionally log the error in a list to be later reviewed by an operator. As shown in FIG. 8, after an action is triggered in step S604, the sample processing apparatus may additionally tag and/or store the image and/or data.

For example, a user may configure the sample processing apparatus to aspirate samples from a pipetting tray and dispense them into a set of wells in a multi-well plate. A robotic arm may move the desired sample tray from a storage location to an active location. A pipetting head may then lower at least one pipette to the sample tray and commence aspirating a plurality of liquid samples, e.g., under the control of the machine vision system. During aspiration, the image acquisition device may capture an image of the pipette tips. After aspiration is complete, the sample processing apparatus may again acquire image(s) of the pipettes, tag them with an identifier and store them in memory. Thereafter, the sample processing apparatus may dispense the sample into a different set of wells, acquire another image of the pipettes, and further testing may be done with the dispensed samples. When the operator reviews the test results, he may notice that the results from one sample or a subset of samples are not what was expected. At that point, he could review the captured images (retrieving them based on an identifier associated with the samples in question) to determine whether the proper volume of sample was aspirated and dispensed. The sample processing apparatus could calculate the volumes in each of the pipettes before and/or after the dispensing step to indicate to the operator whether the pipettor operated properly.

The method described above is one of many possibilities for a sample processing apparatus with vision capability. A number of variations are also within the scope of the present invention and will be apparent to one of skill in the art.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for monitoring a sample handling process, comprising:

associating a liquid sample with a pipette tip;

performing the sample handling process with the liquid sample with respect to the pipette tip, the sample handling process including aspirating or dispensing of the liquid sample with respect to the pipette tip;

using a machine vision system to acquire a 2-dimensional image of at least a portion of the pipette tip before, during or after performance of the sample handling process; and storing the acquired image to allow verification of a presence or absence of a clot associated with the liquid sample during aspirating or dispensing of the liquid sample.

2. The method of claim 1, wherein the step of associating a liquid sample with a pipette tip includes associating liquid samples with a plurality of pipette tips of a multi-channel pipetting head; and the step of using a machine vision system includes acquiring a 2-dimensional image of at least a portion of the plurality of pipette tips.

3. The method of claim 1, further comprising associating the image with an identifier.

4. The method of claim 3, wherein the identifier uniquely identifies the liquid sample.

5. The method of claim 1, further comprising analyzing the image to identify the presence of a clot associated with the pipette tip.

6. The method of claim 5, wherein the analyzing step further includes using the image to determine a volume change of the liquid sample, a presence of an air bubble associated with the liquid sample, or a color associated with the liquid sample.

7. The method of claim 1, wherein the sample handling process comprises dispensing the liquid sample from the pipette tip.

8. A sample handling apparatus, comprising:

at least one pipette tip adapted to hold a liquid sample and allow for aspirating or dispensing of the liquid sample relative to the pipette tip; and a machine vision system having an image acquisition device positioned to acquire a 2-dimensional image of at least a portion of the pipette tip, the machine vision system being adapted to allow verification of a presence or absence of a clot associated with the pipette tip and the aspiration or dispensing of the liquid sample relative to the at least one pipette tip based on the image.

9. The sample handling apparatus of claim 8, wherein the at least one pipette tip includes a plurality of pipette tips.

10. The sample handling apparatus of claim 8, wherein the machine vision system includes an image analyzer adapted to perform an image analysis operation on the image to verify the presence or absence of a clot associated with the pipette tip.

11. The sample handling apparatus of claim 10, wherein the image analyzer is configured to determine a volume of the liquid sample, an existence of the liquid sample, a presence of an air bubble associated with the liquid sample, a color associated with the liquid sample, and/or a presence of a filter based on the image.

12. The sample handling apparatus of claim 8, wherein the image acquisition device includes a CCD camera.

13. The sample handling apparatus of claim 8, wherein the liquid sample is a blood sample and the image is associated with a source of at least a portion of the liquid sample.

14. The sample handling apparatus of claim 13, wherein the source is a person from whom at least a portion of the liquid sample was taken.

15. The sample handling apparatus of claim 8, wherein the machine vision system is adapted to verify that at least a portion of the liquid sample has been dispensed with respect to the pipette tip based on the image.

16. The sample handling apparatus of claim 8, wherein the machine vision system is adapted to verify that at least a portion of the liquid sample has been filtered.

17. The sample handling apparatus of claim 8, further comprising a robotic system adapted to manipulate the pipette tip with the liquid sample.

18. The sample handling apparatus of claim 8, wherein the vision system is adapted to provide input for control of movement of the robotic system.

* * * * *